US00PP29319P2

(12) United States Plant Patent
Eggleton

(10) Patent No.: US PP29,319 P2
(45) Date of Patent: May 29, 2018

(54) ***CONVOLVULUS* PLANT NAMED 'BLUE MOON'**

(50) Latin Name: *Convolvulus hybrida*
Varietal Denomination: Blue Moon

(71) Applicant: Steve Eggleton, Wonga Park (AU)

(72) Inventor: Steve Eggleton, Wonga Park (AU)

( * ) Notice: Subject to any disclaimer, the term of this patent is extended or adjusted under 35 U.S.C. 154(b) by 0 days. days.

(21) Appl. No.: 15/530,797

(22) Filed: Feb. 28, 2017

(51) Int. Cl.
*A01H 5/02* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Cassandra Bright

(57) ABSTRACT

A new and distinct *Convolvulus* cultivar named 'BLUE MOON' is disclosed, characterized by mounding, densely growing plants. Flowers are dark Violet-Blue. The new variety is a *Convolvulus*, normally produced as an outdoor garden or container plant.

2 Drawing Sheets

Figure 1:
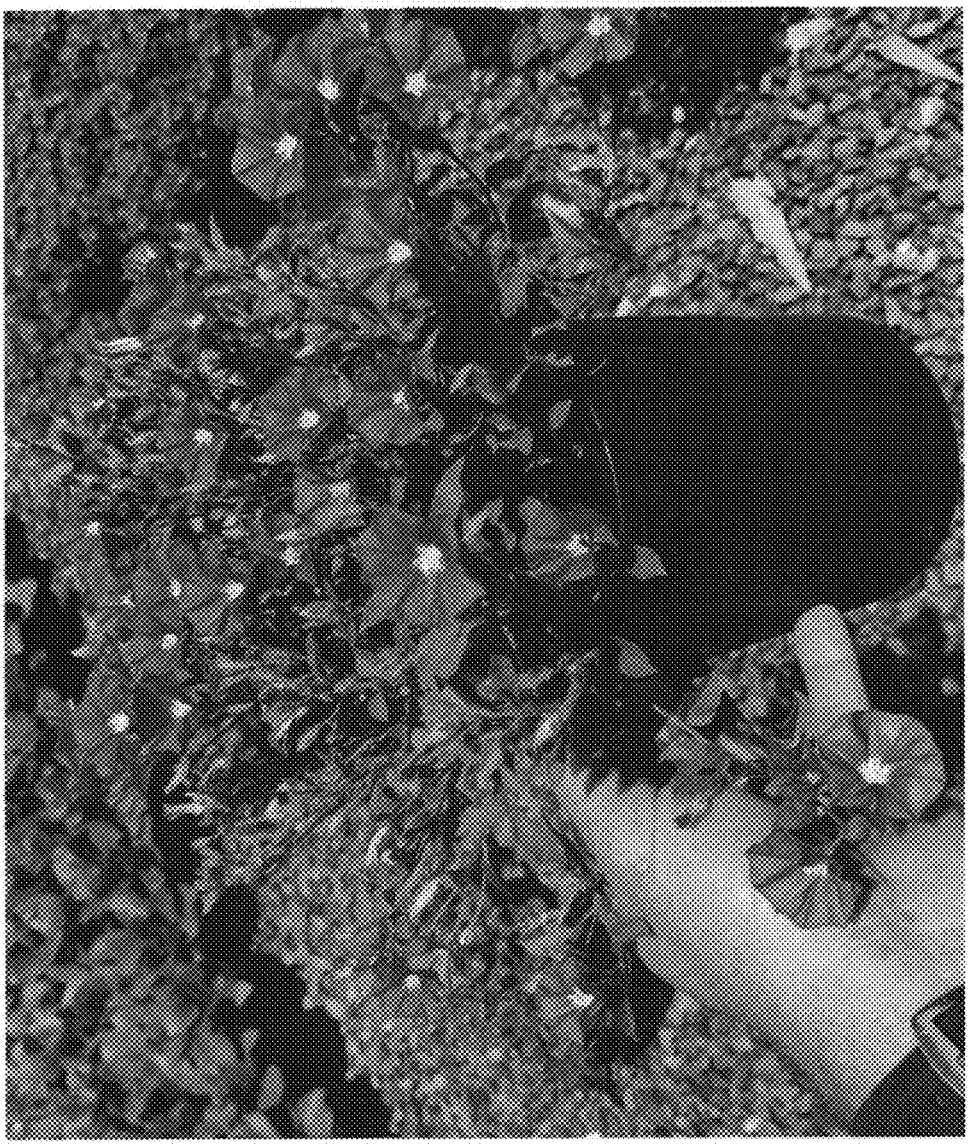

Latin name of the genus and species: *Convolvulus hybrida.*

Variety denomination: 'BLUE MOON'.

BACKGROUND OF THE INVENTION

The new *Convolvulus* cultivar is a product of a planned breeding program, conducted by the inventor, Steve Eggleton, in Wonga Park, Victoria, Australia. The objective of the breeding program was to develop new varieties of *Convolvulus* with compact habits and abundant flowering for commercial ornamental horticultural purposes.

The inventor created an open-pollination breeding program using multiple sources con *Convolvulus* species, including selections from uncultivated populations, landrace varieties or unnamed plants as well as heterogeneous material. The seed parent is the unpatented *Convolvulus* 'Two Moons'. The open-pollination resulting in the new variety occurred during March of 2013. The final selection of this new variety was made November 2014.

Asexual reproduction of the new cultivar was first performed by vegetative stem cuttings. at the same commercial greenhouse in Wonga Park, Australia in November of 2014. Subsequent propagation and growing the plants over a period of several months show the unique characteristics of the new variety to be stable over multiple propagative generations. Plants were first made available to the public Mar. 1, 2016. All plant material made public was originally derived from the inventor.

SUMMARY OF THE INVENTION

The cultivar 'BLUE MOON' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BLUE MOON' These characteristics in combination distinguish 'BLUE MOON' as a new and distinct *Convolvulus* cultivar:

1. Dense plants.
2. Mounding plant form.
3. Abundant dark Violet-Blue flowers.

PARENT COMPARISON

Plants of the new cultivar 'Blue Moon' are similar to plants of 'Two Moons' in most horticultural characteristics, however, plants of the new variety differ in the following:

1. Plants of the new variety are dense, plants of the seed parent variety are sparse.
2. Plant form of the new variety is mounding, plant form of the seed parent is flattened and spreading.
3. Flower color of the new variety is dark Violet-Blue, flower color of the seed parent is white to lavender.

COMMERCIAL COMPARISON

Plants of the new cultivar 'BLUE MOON' can also be comparable to the patented *Convolvulus sabatius*. 'Moroccan Beauty', U.S. Plant Pat. No. 15,104 The two *Convolvulus* varieties are similar in most horticultural characteristics; however, the new variety differs in the following:

1. Plant habit of the new variety is mounding, plant habit of this comparator is flat and spreading.
2. Plants of the new variety are denser than plants of this comparator.
3. Flower color of the new variety is darker than that of this comparator.

BRIEF DESCRIPTION OF THE PHOTOGRAPHS

The accompanying photograph in FIG. 1 illustrates in full color a typical plant of 'BLUE MOON' grown outdoors in Wonga Park, Australia in a 1 liter container. Age of the plant photographed is approximately 20 weeks from a rooted cutting.

Figure 2:
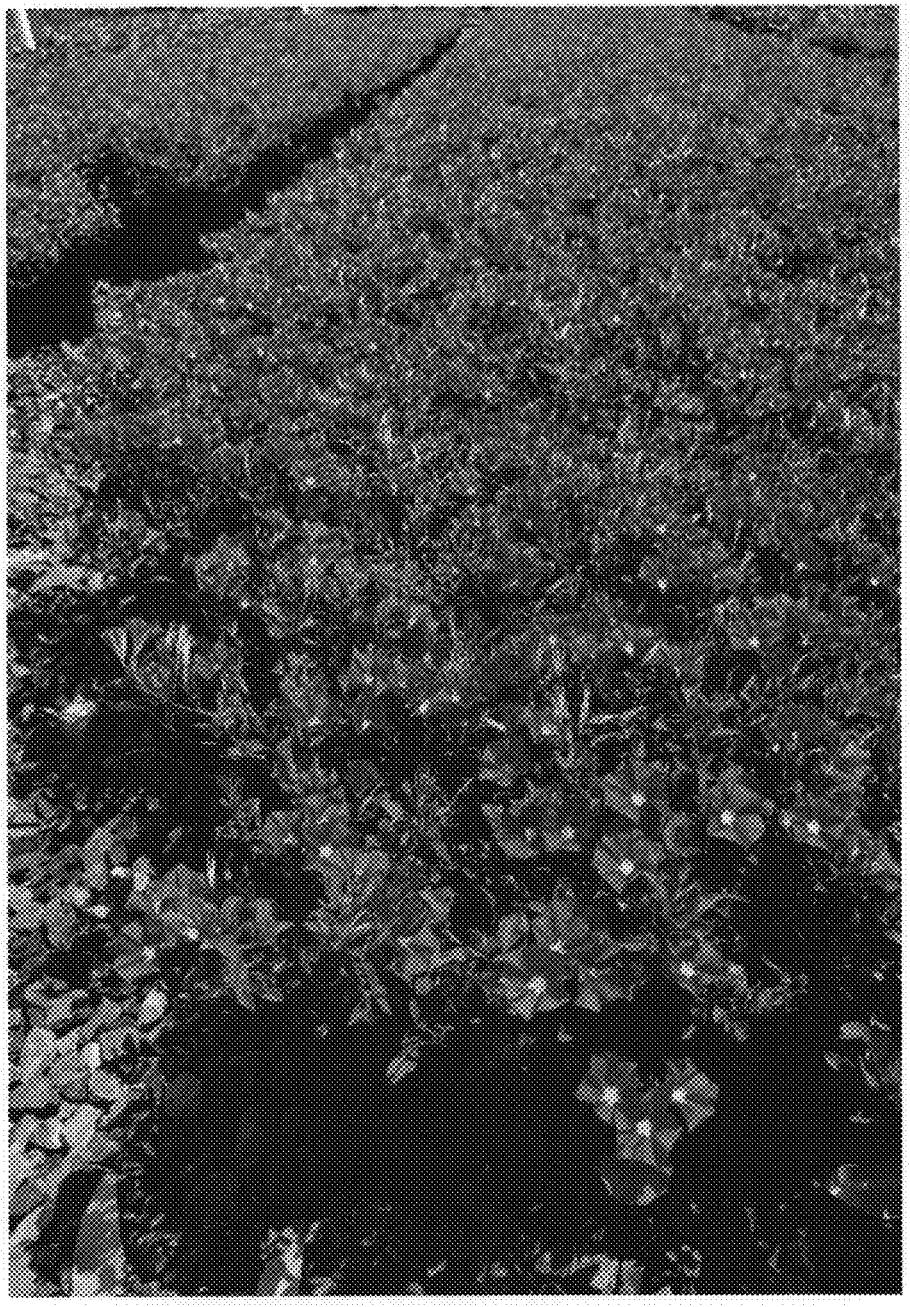

FIG. 2 illustrates several plants of the new variety, grown in liter containers under commercial conditions in Wonga Park, Australia.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'BLUE MOON' plants grown from approximately mid December until mid June in Wonga Park, Australia. The growing temperature ranged from approximately 15° C. to 30° C. during the day and from 8° C. to 25° C. during the night. General light conditions are bright, normal sunlight. Measurements and numerical values represent averages of typical plant types.

Botanical classification: *Convolvulus hybrida* 'BLUE MOON'.

PROPAGATION

Time to initiate roots: About 14 to 21 days at approximately 15 to 22° C.

Root description: Fibrous, spreading and dense. Tan to white, not accurately measured with the R.H.S. chart.

PLANT

Growth habit: Mounding, dense annual.
Pot size of plant described: 1 liter.
Height: Approximately 15 cm.
Plant spread: Approximately 20 cm.
Growth rate: Moderate.
Branching characteristics: Very free-branching.
Branching characteristics: Tight, compact, dense branching.
Length of primary lateral branches: Average 10 cm.
Diameter of lateral branches: 3 mm.
Quantity of primary lateral branches: About 10 to 20.
Characteristics of primary lateral branches.
- *Form*.—Round to oval.
- *Color*.—Near RHS Green 138B.
- *Texture*.—Pubescent.
- *Strength*.—Flexible.

Internode length: Average range 0.7 to 1.2 cm.

FOLIAGE

Leaf:
- *Arrangement*.—Alternate.
- *Quantity*.—Approximately 8 to 12 per branch.
- *Average length*.—Average range from 1.8 to 2.8 cm.
- *Average width*.—Average range from 0.8 to 1.2 cm.
- *Shape of blade*.—Narrow ovate.
- *Apex*.—Acute.
- *Base*.—Rounded.
- *Margin*.—Entire.
- *Texture of top surface*.—Pubescent.
- *Texture of bottom surface*.—Pubescent.
- *Aspect*.—Somewhat undulate and slightly upwardly cupped.
- *Color*.—Young foliage upper side: RHS Green 137C. Young foliage under side: RHS Green 138A. Mature foliage upper side: RHS Green 137C. Mature foliage under side: RHS Green 138A.
- *Venation*.—Upper: Near Yellow-Green 144B. Lower: Near Yellow-Green 144C.
- *Petiole*.—Average Length: Approximately 2 to 3 mm. Diameter: Approximately 1 mm. Color: Near Green 138B. Texture: Densely pubescent.

FLOWER

Natural flowering season: Spring to Autumn in Wonga Park, Australia.

Inflorescence and flower type and habit: Terminal inflorescence. Single rotate funnelform flower.

Rate of flower opening: About 3 days from bud to fully opened flower.

Persistent or self-cleaning: Self cleaning.

Bud:
- *Shape*.—Narrowly conical.
- *Length*.—Approximately 6 mm.
- *Diameter*.—Approximately 2 mm.
- *Color*.—Bud base: RHS White N155B, turning Violet-Blue N189C towards apex.

Flower size:
- *Diameter*.—Average 2.2 cm.
- *Depth*.—1.8 cm.

Corolla/petals:
- *Arrangement*.—Single flower with 5 completely fused petals. Outward and upwardly facing.
- *Length*.—Approximately 1.2 cm.
- *Width*.—Approximately 0.8 cm.
- *Quantity*.—5 petals.
- *Texture*.—Glabrous.
- *Apex*.—Broad acute.
- *Margin*.—Entire.

Color:
- *When opening*.—Upper surface: RHS Violet-Blue N89B, base near White N155B. Lower surface: Apex near Violet-Blue N89B, mid-section near 91A, base near White N155B.
- *Fully opened*.—Upper surface: RHS Violet-Blue N89C, base near White N155B. Lower surface: Apex near Violet-Blue N89B, mid-section near 90C, base near White N155B.

Calyx/sepals:
- *Description*.—5 sepals basally fused to form calyx.
- *Calyx length*.—6 mm.
- *Calyx width*.—3 mm.

Sepals:
- *Shape*.—Deltoid.
- *Length*.—6 mm.
- *Width*.—About 1.5 mm.
- *Apex*.—Acute.
- *Base*.—Fused.
- *Margin*.—Entire.
- *Texture*.—Pubescent all surfaces.
- *Color*.—Upper Surface: RHS Green N138A. Lower Surface: RHS Green N138B.

Bracteoles:
- *Quantity*.—2 per petiole.
- *Shape*.—Lanceolate.
- *Length*.—4 mm.
- *Width*.—About 1 mm.
- *Apex*.—Acute.
- *Base*.—Truncate.
- *Margin*.—Entire.
- *Texture*.—Pubescent all surfaces.

*Color*.—Upper Surface: RHS Green N138A. Lower Surface: RHS Green N138B.

Peduncle:

*Length*.—Approximately 0.5 cm.

*Diameter*.—Approximately 0.3 cm.

*Color*.—RHS Green 138A.

*Texture*.—Pubescent.

*Strength*.—Flexible.

REPRODUCTIVE ORGANS

Stamens:

*Number*.—Approximately 5.

*Filament length*.—Adenate to corolla, non attached segment about 4 mm.

*Filament color*.—Near While N155B.

Anthers:

*Shape*.—Sagitate.

*Length*.—Less than 0.5 mm.

*Color*.—RHS White N155B.

*Pollen*.—Color: Near RHS White N155B. Quantity: Moderate.

Pistil:

*Number*.—1 per flower.

*Length*.—About 8 mm.

*Style*.—Length: 6 mm. Color: Near RHS Yellow-Green 145D.

*Stigma*.—Shape: Linear. Color: Near RHS White N155B. Ovary Color: Near RHS Yellow-Green 145D.

OTHER CHARACTERISTICS

Seeds and fruits: Not observed to date.

Disease/pest resistance: Neither resistance nor susceptibility observed.

Temperature tolerance: USDA Zone 8.

What is claimed is:

1. A new and distinct cultivar of *Convolvulus* plant named 'BLUE MOON' as herein illustrated and described.

* * * * *